United States Patent [19]

Chapas et al.

[11] Patent Number: 4,820,295
[45] Date of Patent: Apr. 11, 1989

[54] ABSORBENT BODY WITH FLUID TRANSPORT MEANS

[75] Inventors: Richard B. Chapas, East Windsor; Pramod Mavinkurve, Kendall Park, both of N.J.

[73] Assignee: Personal Products Company, Milltown, N.J.

[21] Appl. No.: 13,475

[22] Filed: Feb. 11, 1987

Related U.S. Application Data

[63] Continuation-in-part of Ser. No. 858,883, Apr. 24, 1986, abandoned, which is a continuation of Ser. No. 530,320, Sep. 8, 1983, abandoned.

[51] Int. Cl.[4] ............................................. A61F 13/16
[52] U.S. Cl. ................................ 604/385.1; 604/379
[58] Field of Search ............... 604/358, 378, 379, 380, 604/384–385 R; 128/155

[56] References Cited

U.S. PATENT DOCUMENTS

| | | | |
|---|---|---|---|
| 2,047,054 | 7/1936 | Beyer, Jr. ........................ | 604/385 R |
| 2,747,575 | 5/1956 | Mercer ............................ | 604/385 R |
| 2,939,461 | 6/1960 | Joa ................................... | 604/374 |
| 3,230,955 | 1/1966 | Joa et al. ......................... | 604/366 |
| 3,295,526 | 1/1967 | Sabee ............................... | 604/366 |
| 3,364,931 | 1/1968 | Hirsch ............................. | 604/366 |
| 3,545,441 | 12/1970 | Gravdahl ......................... | 604/385.1 |
| 3,559,648 | 2/1971 | Mason, Jr. ....................... | 604/375 |
| 3,592,194 | 7/1971 | Duncan ........................... | 604/375 |
| 4,041,950 | 8/1977 | Jones, Sr. ......................... | 604/378 |
| 4,184,498 | 1/1980 | Franco ............................. | 604/379 |
| 4,212,302 | 7/1980 | Karami ............................ | 604/374 |
| 4,410,324 | 10/1983 | Sabee ............................... | 604/385.2 |
| 4,413,996 | 11/1983 | Taylor ............................. | 604/382 |
| 4,449,979 | 5/1984 | Holtman .......................... | 604/379 |
| 4,699,823 | 10/1987 | Kellenberger et al. ............ | 604/378 |

FOREIGN PATENT DOCUMENTS 2133987 8/1984 United Kingdom ............... 604/358

*Primary Examiner*—John D. Yasko
*Assistant Examiner*—Sharon Rose

[57] ABSTRACT

An absorbent body is provided for absorbing body fluids. The body is generally planar and elongated and is surrounded by a substantially uniformly compressed peripheral edge. Fluid striking the absorbent body at a point in proximity to the densified peripheral edge is transported rapidly away from said point.

5 Claims, 3 Drawing Sheets

U.S. Patent    Apr. 11, 1989    Sheet 1 of 4    4,820,295
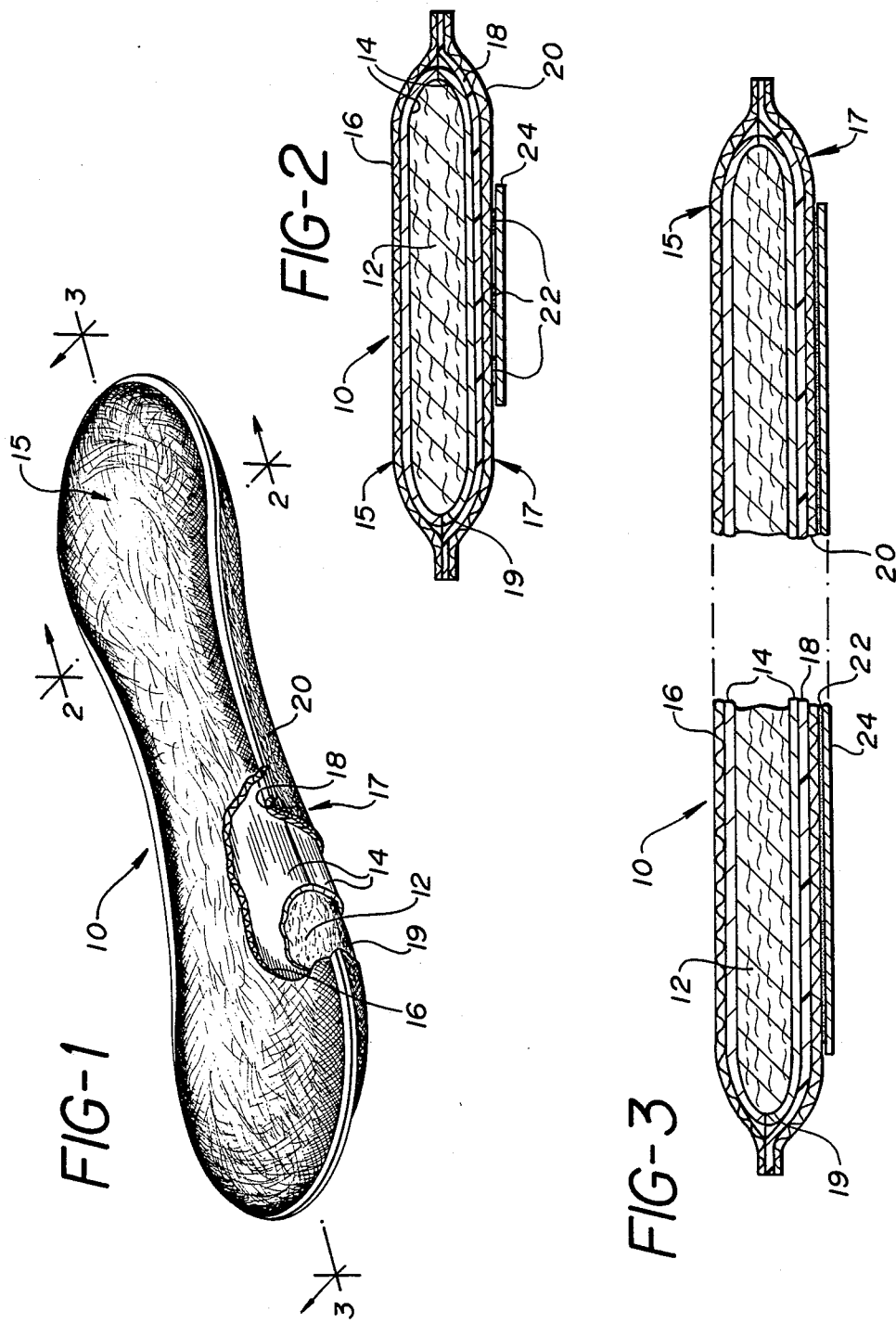

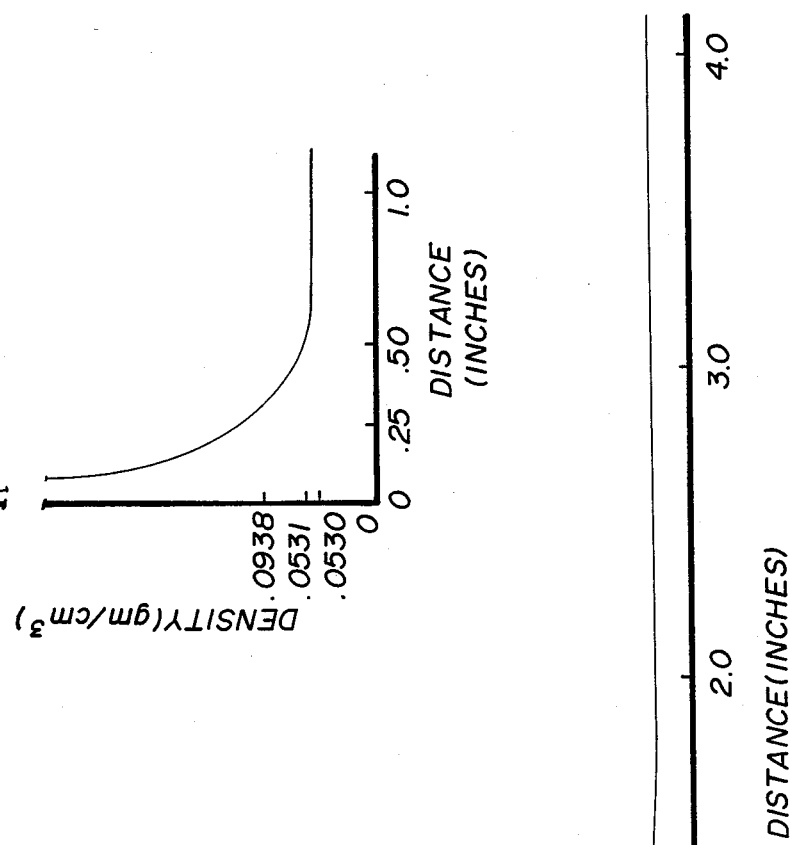
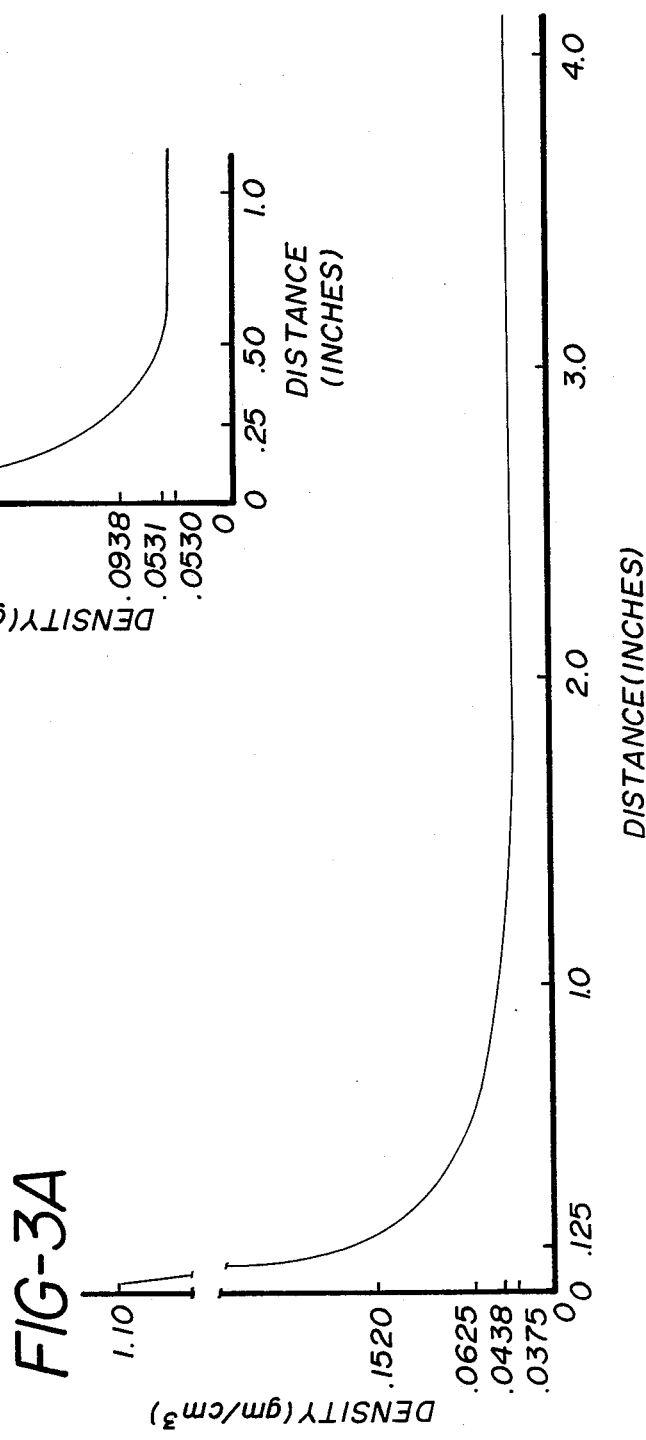
FIG-2A
FIG-3A

BODY SIDE    GARMENT SIDE

BODY SIDE    GARMENT SIDE

ABSORBENT BODY WITH FLUID TRANSPORT MEANS

This is a continuation-in-part of/application Ser. No. 858,883 filed Apr. 24, 1986, now abandoned which was a continuation of application Ser. No. 530,320 filed Sept. 8, 1983, now abandoned.

BACKGROUND OF THE INVENTION

This invention relates to providing a pad of fibrous absorbent material for absorbing body fluids and in particular relates to an absorbent pad for use in such products as sanitary napkins, panty liners, diapers and the like.

In general, such products comprise one or more layers of a core of hydrophilic material such as wood pulp, rayon tissue or the like. The hydrophilic material, generally fibrous in form, is provided as a pad having a rectangular or oblong shape or in some cases, a shape designed to more closely fit the anatomy of the wearer. The pad is usually provided with an enveloping cover pervious to body fluids on the side of the pad designed to be placed against the body and impervious to such fluids on the side facing away from the body. The object of such body fluid impervious cover is, of course, to protect the clothing from staining and wetting.

In the main, such products have satisfactorily performed their function of absorbing and retaining body fluids and preventing staining and wetting of the wearer's clothing. Generally, when the product is properly placed and retained by the wearer in its intended position, body fluid is directed at or near the center of the product and distributes, by means of liquid wicking, throughout the absorbent medium. Unfortunately, in a significant number of cases, the product is misplaced, either initially by the user or because of displacement caused by the activities of the user. In these circumstances, body fluid will strike the pad off-center and closer to the peripheral edges of the pad. It is believed that this off-center disposition of body fluid is the cause of a significant number of failures associated with the use of these products i.e., body fluid staining and wetting the clothing of the wearer.

Accordingly, there is a need for providing a pad for body fluid absorbent products which protects the user from the disadvantageous effects of product misplacement.

SUMMARY OF THE INVENTION

In accordance with the teachings of this invention an absorbent pad for a body fluid absorbent product is provided which alleviates the problem of wetting or staining the clothing of the wearer by body fluid which strikes the pad in proximity to the peripheral edges.

This feature is accomplished by providing, in a pad-like body of fibrous absorbent material, a substantially uniformly compressed peripheral edge. Preferably such compressed edge is integral with the bulk of the pad and is densified to a bulk density of at least about ten times that of the least dense portion of the pad. More preferably, the peripheral edge of the pad is at least twenty times that of the least dense portion of the pad.

In a preferred embodiment, the pad is provided with a density gradient wherein the density gradually increases from the least dense portion of the pad toward the periphery of the pad. The gradual increase however becomes a sharp increase as the periphery is approached and ultimately the density of the peripheral edge is that prescribed above. It is preferred that the compressed peripheral edge entirely circumscribes the pad although a substantial realization of the benefits of this invention are accrued when only a portion of the peripheral edge is of the herein prescribed density. In a specific embodiment, all or a portion of the edge of the pad is overlaid with a fluid impervious cover to shield the user's clothing from wetting.

It has been discovered that by following the teachings of this invention, fluid reaching a point at the peripheral edge of the pad is rapidly transported along the periphery and away from such point. This transport of fluid has been experimentally observed in in-vitro tests in which product incorporating such pad show far fewer incidence of failing i.e., body fluid appearing on the outer surface of such products.

BRIEF DESCRIPTION OF THE DRAWINGS

FIG. 1 is a perspective view of a sanitary napkin as a first embodiment of this invention with parts removed therefrom to show internal detail;

FIG. 2 is a transverse, cross-sectional view of the sanitary napkin of FIG. 1 taken along line 2—2 of FIG. 1;

FIG. 2a is a graphical representation of the pad density gradient in the transverse direction of the pad extending inward from the outer boundary of the peripheral edge;

FIG. 3 is a longitudinal, cross-sectional view of the sanitary napkin of FIG. 1, taken along line 3—3 of FIG. 1;

FIG. 3a is a graphical representation of the pad density gradient in the longitudinal direction of the pad, extending inward from the outer boundary of the peripheral edge;

DETAILED DESCRIPTION OF THE INVENTION

Figure 7:
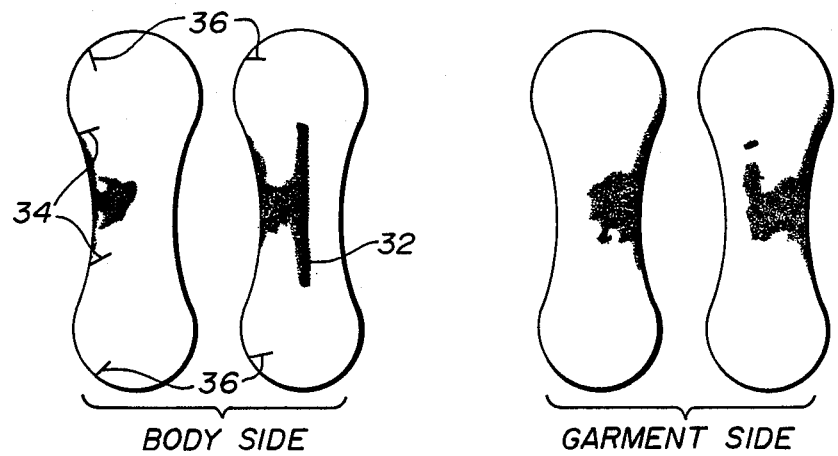
FIGS. 5-7 are photographs of pads incorporating the teaching of this invention.

Referring now to FIG. 1, illustrated there, in perspective view, is a sanitary napkin 10 incorporating the teachings of this invention. FIGS. 2 and 3 illustrate the napkin 10 in transverse and longitudinal cross sections, respectively.

The napkin consists of an absorbent element 12 which is shown in the form of a generally planar pad. The choice of materials for use in the pad of this invention is not critical. It is important however, that the pad employed be capable of densification in the manner prescribed herein and that such densification result in the fluid transport properties described in greater detail hereinafter.

Preferably, the pad comprises loosely associated absorbent hydrophilic material such as cellulose fibers, e.g., wood pulp. regenerated cellulose or cotton fibers. Such fibers may be chemically or physically modified and the pad may include such fibers in combination with other materials, both natural and synthetic, such as hydrophilic foams, hydrophilic polymers or the like. A material of choice is wood pulp which is inexpensive, readily available and lends itself well to the densification specified by the teachings of this invention.

The pad 12, as illustrated in FIGS. 1-3, is wrapped in a tissue wrap 14 which is provided to aid in holding the product together during manufacturing and to help retain the shape of the finished product. Overlying a first major surface 15 of the napkin 10 i.e., the side of the napkin to be worn against the body of the user, is a body fluid pervious cover 16. The cover 16 may be any woven or nonwoven material pervious to body fluid striking its surface, such covers being well known in the art. In a preferred embodiment, the cover comprises thermoplastic material capable of being fusibly sealed to another element of the napkin, e.g., by heat, pressure, sonic sealing, or the like.

A material of choice for the cover is a fabric comprising heat bondable polyester/polyethylene conjugate fibers. Such conjugate fibers are fibers which comprise a polyester core surrounded by a sheath of polyethylene. preferably, the conjugate fibers employ high density polyethylene, that is, linear polyethylene that has a density of at least 0.94 gm/cc and a Melt Index (as determined by ASTMD-1288E method, employing the parameters of 190° C. and 2160 gms.) of greater than 1, preferably greater than about 10, and more preferably from about 20 to about 50. The fibers may comprise from about 40 to about 60 percent, by weight polyester, with the remainder being polyethylene. Such fibers may be used in deniers of from 1 to about 6 and may be from about ½ inch (1.27 cm.) to about 3 to 4 inches (7.62 to 10.16 cm.) long. The fabric comprising such fibers is stabilized by applying heat thereto under essentially zero pressure whereby thermal bonding takes place without destroying the integrity of the fibers.

Overlying the second major surface 17 of the pad 12 (the side worn away from the body of the user) and at least a part of the edges 19 of pad 12 is a body fluid impervious layer 18. The layer 18 is provided to preclude body fluid from passing onto an undergarment and may be constructed of any material suitable for this purpose. For example, the layer 18 may be a polymeric film such as polyethylene, polypropylene, or cellophane or may be a normaly fluid pervious material that has been treated to be impervious such as a fluid repellant paper. Advantageously, the layer 18 is a heat bondable material such as polyethylene which can be bonded to layer 16 to completely enclose pad 12.

In a preferred configuration layer 20, which comprises a nonwoven fabric constitutes the outer layer of the garment side of the napkin 10. This fabric outer layer is provided for aesthetic purposes and for its soft feel.

As best viewed in FIGS. 2 and 3, the garment surface of the napkin 10 is provided with pressure sensitive adhesive elements 22 for adhering the napkin to the crotch portion of the wearer's undergarment. As shown in this specific embodiment these adhesive elements 22 are in the form of three longitudinally extending bands although it will be understood by those skilled in the art that many variations in the number and shape of these adhesive elements are possible. The pressure-sensitive adhesive may be any of the already known compositions suitable for this purpose including, for example, the water based pressure-sensitive adhesives such as the acrylate adhesives, e.g., vinyl acetate-2 ethyl hexyl acrylate copolymer which are generally combined with tackifiers such as, for example, ethylene amine. Alternatively, the adhesive may comprise the rapid setting thermoplastic (hot melt) adhesives such as block copolymers exemplified by styrene and butadiene/styrene copolymers. The adhesive elements may also comprise a two-sided adhesive tape.

The adhesive areas are protected by a release strip 24 to avoid undesired adhesion prior to use. The release strip 24 may be made of any suitable sheet-like material which adheres with sufficient tenacity to the adhesive elements 22 to remain in place, but which can be readily removed when the napkin 10 is to be used. A particularly useful material is a semi-bleached kraft paper, the adhesive contacting side of which has been silicone coated to provide for easy removal from the adhesive just prior to use.

Referring now to FIG. 2a, shown graphically is a plot of density as the ordinate versus the transverse distance along the line 2—2 taken through pad 12 illustrated in FIG. 2, as the abscissa. As can be seen, the density of the pad increases gradually and at a slow rate from a point in the pad of least density toward the outer periphery of the pad. In the embodiment illustrated, the least dense portion of the pad, with respect to the transverse and longitudinal centerlines, is the center of the pad. It should be understood however that this embodiment is merely exemplary and that, for example, a compressed central channel may be provided in the pad, in which case the least dense portion of the pad would be off-center.

In accordance with the teachings of this invention, and as best illustrated in FIG. 2a, as the periphery of the pad is closely approached, the density of the pad increases sharply to the peripheral edge where the density is at least ten times that of the least dense portion and preferably, at least twenty times. For the embodiment illustrated in the drawings the density of the peripheral edge is 1.10 gm/cc, and is 20 times that of the least dense portion of the pad, which density is about 0.05 gm/cc. It will be understood by those skilled in the art that the density being referred to herein is the local bulk density of the pad, i.e., the weight of a unit volume pad, including in such unit volume the interstitial void volume such as exists between wood pulp fibers, for example.

Referring now to FIG. 3a, illustrated there is a plot of density as the ordinate verses longitudinal distance along the line 3—3, taken through pad 12 illustrated in FIG. 3 as the abscissa. Once again it can be seen that the density increases gradually at a slow rate from the least dense portion of the pad (in this embodiment, the center) toward the periphery. As the periphery is closely approached the density increases sharply to the values prescribed herein for the peripheral edge of the pad.

In a preferred embodiment, the high density peripheral edge area extends inwardly from the extreme periphery a distance of at least 0.1 cms and preferably at least 0.2 cm. Within the peripheral edge area, the densities are substantially uniform and within the prescribed values of at least ten times that of the least dense area of the pad and preferably at least twenty times that of the least dense areas. While substantial benefit is gained by having only the longitudinally central peripheral areas of the pad provided with the prescribed high density, it is preferable that the entire peripheral areas of the pad be so densified.

The advantages of this invention will be best understood by considering the following examples taken together with FIGS. 4-7 of the appended drawings.

COMPARATIVE EXAMPLE

A pad is provided comprising 8.5 gms of southern pine semi-bleached wood pulp and having the dimensions of 19.6 cm long, 6.6 cm wide, and 1.65 cm thick. The pad, representative of prior art pads utilized in sanitary napkins now on the market, has an essentially uniform density of 0.50 gm/cc. The pad is covered with a tissue wrap on its side.

To simulate the disadvantageous effect of off-center liquid depositions, liquid is deposited on the body side of the pad at a point 1.27 cms inward from a longitudinal edge of the pad and on the transverse center line. The liquid deposited is an ersatz menstrual fluid which comprises 1% by weight aqueous NaCl solution and 0.2%, by weight, of surface active agent to emulate the surface tension of menstrual fluid, i.e., approximately 50 dynes/cm. The surface active agent used is poly(ethylene oxide)-poly(propylene oxide) block copolymer sold by the Wyandette Chemical Corporation of Michigan, U.S.A. under the trade name Pluronic. The liquid also comprises a red dye. The liquid is deposited at the above described point of liquid deposition by placing the tip of a 50 cubic centimeter burret as close as possible to the pad without actually touching the pad. Ten cubic centimeters of the fluid are then deposited as quickly as can be discharged from the burret (utilizing a full burret with the stop clock in the completely open position).

It is observed that the liquid tends to remain at the point of deposition with only very slow migration to adjacent parts of the pad. After a substantial portion of the ten cubic centimeters of liquid has been deposited, the liquid tends to puddle and run off the surface of the pad. Such a condition, in a complete napkin, would cause a napkin failure; i.e., menstrual fluid wetting the undergarment of the user. This is true even when the longitudinal edges of the pad are covered by a fluid impervious cover such as is illustrated in FIGS. 1–3 in that the puddled fluid will run over the edge of the impervious layer and wet the user's undergarment.

Figure 4:
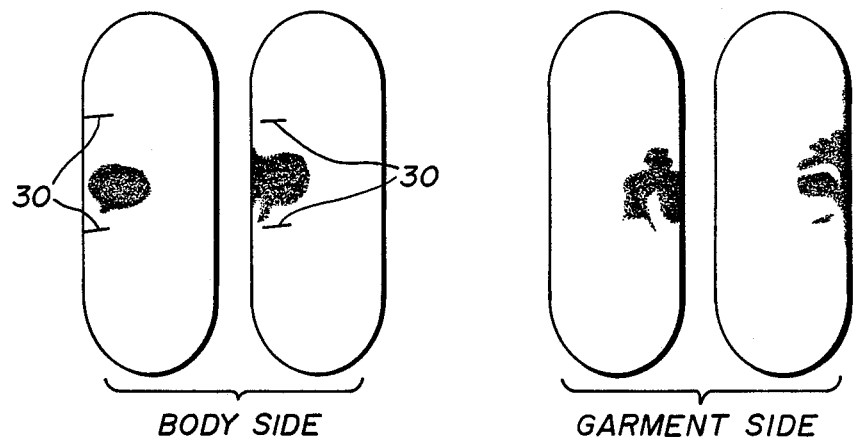
FIG. 4 is a photograph of a prior art pad illustrating the disadvantageous fluid distribution properties which this invention is directed toward alleviating.

FIG. 4 is a photograph of two of the above pads after deposition of fluid showing both the body sides and the garment sides. The lines 30 denote the maximum travel of the liquid five minutes after liquid deposition.

EXAMPLE 1

A series of pads are provided having the general configuration of pad 12 illustrated in FIGS. 1–3. The pads, comprising southern pine semi-bleached wood pulp measure 19.2 cm long 5.1 cm wide at the longitudinal center, have the density gradient set out in FIGS. 2a and 3a.

Figure 5:
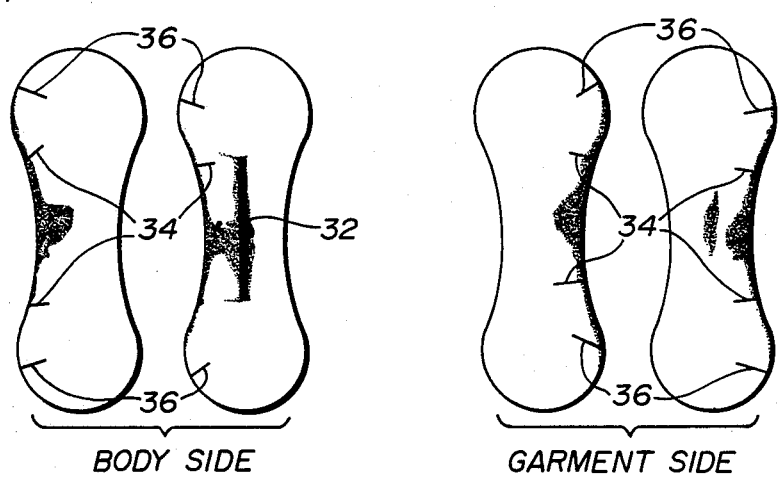

The pads are subjected to the same deposition of ersatz menstrual as is described in connection with the comparative example. FIG. 5 illustrates the fluid transport properties of a first set of such pads showing both the body side and the garment side of the pads. The pads shown in the FIG. 5 are completely enveloped with a tissue wrap as is illustrated in FIGS. 1–3. The pad on the right is identical to that of FIGS. 1–3 whereas the pad of the left is provided with a compressed central channel 32. Accordingly, the least compressed parts of this pad along a transverse, longitudinally centered line is at a point between the compressed central channel and the compressed peripheral area. The lines 34 represent the spread of liquid immediately after deposition of the liquid. Lines 36 represent the spread of liquid five minutes after liquid deposition. As can be seen from these photographs, unlike the prior art pads, there is a rapid and advantageous transport of liquid away from the point of deposition. By observation it is noted that the transport is rapid enough to prevent liquid puddling at the point of deposition.

EXAMPLE 2

Figure 6:
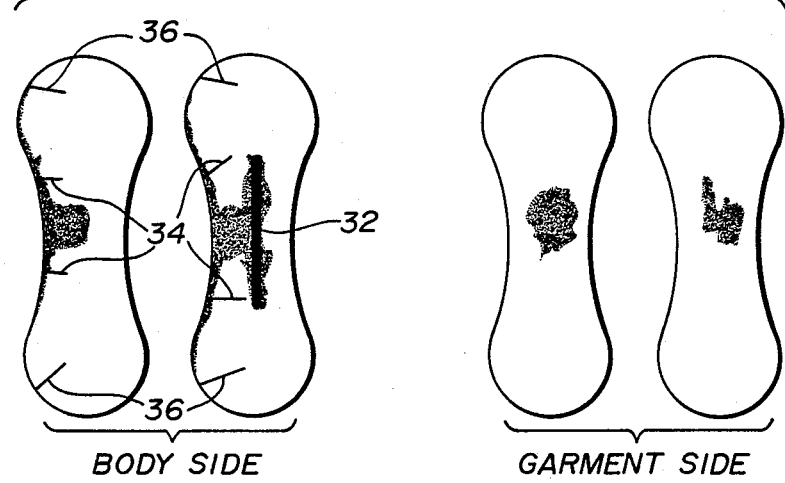

A series of pads are provided, identical to those of Example 1 with the exception that only the body sides of the pads are covered with tissue. FIG. 6 illustrates the spread of liquid deposited thereon and again it is noted that rapid transport of liquid results.

EXAMPLE 3

A series of pads are provided identical to those of Example 1 with the exception that no tissue cover is employed. FIG. 7 illustrates the spread of liquid deposited thereon and again it is noted that rapid transport of liquid results.

EXAMPLE 4

To quantify the results exhibited by FIGS. 4–7, the deposition of fluid was carried out, as described in Example 1–3 and in the comparative example, for a number of pads having the various described configurations. The initial spread of liquid along the peripheral edge of the pad was measured immediately after deposition of liquid and then five minutes thereafter. The arithmetic average of these values for each type of pad are reported in Table 1 below.

TABLE 1

| Pad Type | | No. of Pads | Initial Length (in.) | Length After 5 Mins. (in.) |
| --- | --- | --- | --- | --- |
| Comparative Example | | 9 | 1.44 | 2.35 |
| Example 1 - | Tissue on Both Sides | 12 | 2.75 | 6.27 |
| Example 2 - | Tissue on Body Side Only | 15 | 2.76 | 6.60 |
| Example 3 - | No Tissue | 15 | 2.28 | 7.05 |

As can be seen from Table 1, the pads of Examples 1–3 incorporating the teachings of this invention all exhibit a greater initial length, i.e., more rapid liquid transport, than the prior art pad of the comparative example. After five minutes the contrast is even greater.

EXAMPLE 5

A series of pads of Example 1 are incorporated into a sanitary napkin having the general structure shown in FIGS. 1–3. The napkins are then tested on a Dynamic Form Testing apparatus, the test comprising suspending the napkin to be tested across a rubber mold which simulates the female form. The form is set in motion by means of a set of gears, cams and rods and ersatz menstrual fluid is allowed to drip onto the napkin to closely approximate in-use conditions. The fluid is applied at a rate of about 0.3 cc/min. and the form is operated at a speed of 60 cycles/min. and the form is operated at a speed of 60 cycles/min. The fluid capacity of the napkin under dynamic conditions is measured by the total volume of fluid applied at the time of failure, i.e., the time at which spotting is noted on the underside of the napkin.

A second series of napkins incorporating the prior art pad described in the comparative example are similarly tested. The results of these tests are set out in Table 2 below.

TABLE 2

| Pad Type | No. of Pads | Pad Weight (cm) | Total Napkin wt. | Dynamic Capacity (cc.) |
|---|---|---|---|---|
| Comparative Example | 6 | 8.53 | 12.9 | 50.9 |
| Example 1 | 6 | 8.62 | 11.0 | 84.4 |

As can be seen from Table 2, the capacity of the napkin as measured by this test is substantially increased.

The absorbent bodies of this invention may be manufactured by several alternative methods which will occur to one skilled in the art. For example, a pad may be provided which is thicker at the peripheral portions than at the central portions and then compressed to a uniform thickness to produce the prescribed density gradient. Preferably, a pad is first provided of uniform thickness and is compressed in a mold to produce a compressed pad wherein the peripheral portions are thinner and denser than the central portions to result in the prescribed gradient. The pressure applied to the pad may be uniform or excessive pressure may be brought to bear against the extreme peripheral edges. Such excessive pressure may be applied, for example, by the use of die cutters which cut the pad to the desired shape while simultaneously applying the excessive pressure which in cooperation with the contours of the mold, produce the herein prescribed pressure gradient.

We claim:

1. An absorbent body of fibrous material for absorbing body fluids, said body being generally planar and elongated and having a substantially uniformly compressed peripheral edge extending about essentially the entire periphery of the body;

said peripheral edge having a bulk density of at least ten times greater than the least dense portion of the body, said dense peripheral edge extending inwardly from the extreme periphery for a distance of at least 0.1 cm;

said body provided with a transverse density gradient, said longitudinal gradient extending from a point of least density longitudinally toward said compressed peripheral edge with said density increasing toward said peripheral edge at an increasing rate said body provided with a transverse density gradient, said transverse gradient extending from a point of least density transversely toward said compressed peripheral edge and said transverse density increasing toward said peripheral edge at an increasing rate;

whereby body fluid striking the body at a point in proximity to the peripheral edge will be transported rapidly away from said point.

2. The absorbent body of claim 1 wherein said transverse gradient extends from a point at least 0.25 inches from the peripheral edge.

3. The absorbent body of claim 2 wherein said transverse gradient extends from a point at least 0.5 inches from said peripheral edge.

4. The absorbent body of claim 1 wherein said longitudinal gradient extends from a point at least 1.0 inches from said peripheral edge.

5. The absorbent body of claim 4 wherein said longitudinal gradient extends from a point at least 1.5 inches from said peripheral edge.

* * * * *

UNITED STATES PATENT AND TRADEMARK OFFICE
CERTIFICATE OF CORRECTION

PATENT NO.   :   4,820,295
DATED        :   April 11, 1989
INVENTOR(S)  :   Richard B. Chapas et al.

It is certified that error appears in the above-identified patent and that said Letters Patent is hereby corrected as shown below:

In claim 1, column 8, line 8, delete "transverse" and insert --longitudinal--.

Signed and Sealed this

Twenty-third Day of January, 1990

Attest:

JEFFREY M. SAMUELS

Attesting Officer        Acting Commissioner of Patents and Trademarks